(12) United States Patent
Millet

(10) Patent No.: US 11,950,616 B2
(45) Date of Patent: *Apr. 9, 2024

(54) NON-VASOCONSTRICTING ENERGY-PROMOTING COMPOSITIONS CONTAINING KETONE BODIES

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/320,657

(22) Filed: May 14, 2021

(65) Prior Publication Data

US 2021/0267247 A1 Sep. 2, 2021

Related U.S. Application Data

(63) Continuation-in-part of application No. 16/849,901, filed on Apr. 15, 2020, now Pat. No. 11,033,553.

(60) Provisional application No. 62/864,989, filed on Jun. 21, 2019.

(51) Int. Cl.
| | |
|---|---|
| *A61K 36/258* | (2006.01) |
| *A23L 2/52* | (2006.01) |
| *A23L 33/105* | (2016.01) |
| *A61K 31/12* | (2006.01) |
| *A61K 31/335* | (2006.01) |
| *A61K 31/52* | (2006.01) |
| *A61K 31/522* | (2006.01) |

(52) U.S. Cl.
CPC .............. *A23L 33/105* (2016.08); *A23L 2/52* (2013.01); *A61K 31/522* (2013.01)

(58) Field of Classification Search
CPC .... A61K 36/258; A61K 31/52; A61K 31/335; A61K 21/12
USPC ............... 514/263.34, 456, 675; 424/36, 258
See application file for complete search history.

(56) References Cited

U.S. PATENT DOCUMENTS

| | | |
|---|---|---|
| 2,238,149 A | 4/1941 | Aeckerle |
| 2,976,073 A | 3/1961 | Russell et al. |
| 4,627,808 A | 12/1986 | Hughes |
| 4,771,074 A | 9/1988 | Lammerant et al. |
| 4,997,976 A | 3/1991 | Brunengraber et al. |
| 5,093,044 A | 3/1992 | Wretlind et al. |
| 5,100,677 A | 3/1992 | Veech |
| 5,116,868 A | 5/1992 | Chen et al. |
| 5,288,512 A | 2/1994 | Seiden |
| 5,292,774 A | 3/1994 | Hiraide et al. |
| 5,654,266 A | 8/1997 | Chen et al. |
| 5,700,670 A | 12/1997 | Yamagishi et al. |
| 6,207,856 B1 | 3/2001 | Veech |
| 6,217,915 B1 | 4/2001 | Luchansky et al. |
| 6,232,345 B1 | 5/2001 | Hiraide et al. |
| 6,316,038 B1 | 11/2001 | Veech |
| 6,323,237 B1 | 11/2001 | Veech |
| 6,380,244 B2 | 4/2002 | Martin et al. |
| 6,613,356 B1 | 9/2003 | Vlahakos |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,925,164 B1 | 3/2018 | Hashim |

(Continued)

FOREIGN PATENT DOCUMENTS

| | | |
|---|---|---|
| CN | 86108978 A | 11/1987 |
| CN | 1256629 A | 6/2000 |

(Continued)

OTHER PUBLICATIONS

International Preliminary Report on Patentability received for PCT Patent Application No. PCT/US2018/062093, dated Jun. 4, 2020, 6 pages.

International Preliminary Report on Patentability received for PCT Patent Application No. PCT/US2021/045186, dated Mar. 9, 2023, 7 pages.

International Preliminary Report on Patentability received for PCT Patent Application No. PCT/US2021/050302, dated Mar. 2, 2023, 8 pages.

(Continued)

*Primary Examiner* — Raymond J Henley, III
(74) *Attorney, Agent, or Firm* — Workman Nydegger

(57) ABSTRACT

An energy-promoting composition includes an exogenous ketone body component that provides a source of caloric energy, a vasodilator component, a stimulant component, such as caffeine, and optionally a nootropic component. In most if not all cases, the vasodilator, stimulant, and nootropic components do not themselves provide a source of caloric energy but may increase metabolism of available caloric energy. The separate components beneficially and synergistically interact with one another to enhance the overall energy-promoting effect of the composition more rapidly and to a greater degree than if one or more of the components are omitted. The energy-promoting composition is also formulated to minimize the crash effect common to stimulants such as energy drinks.

20 Claims, 1 Drawing Sheet

(56) References Cited

U.S. PATENT DOCUMENTS

| | | |
|---|---|---|
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |
| 10,292,592 B2 | 5/2019 | Marshall et al. |
| 10,292,952 B2 | 5/2019 | Millet |
| 10,512,615 B1 | 12/2019 | Millet |
| 10,588,876 B2 | 3/2020 | Millet |
| 10,588,877 B2 | 3/2020 | Arnold |
| 10,596,128 B2 | 3/2020 | Millet |
| 10,596,129 B2 | 3/2020 | Millet |
| 10,596,130 B2 | 3/2020 | Millet |
| 10,596,131 B2 | 3/2020 | Millet |
| 10,660,958 B2 | 5/2020 | Clarke |
| 10,736,861 B2 | 8/2020 | Millet |
| 10,792,269 B2 | 10/2020 | Hashim |
| 10,925,843 B2 | 2/2021 | Millet |
| 10,973,786 B2 | 4/2021 | Millet |
| 10,980,764 B1 | 4/2021 | D'Agostino et al. |
| 10,980,772 B2 | 4/2021 | Millet |
| 11,020,362 B2 | 6/2021 | Millet |
| 11,033,553 B2 * | 6/2021 | Millet ................. A23L 2/68 |
| 11,103,470 B2 | 8/2021 | Millet |
| 11,185,518 B2 | 11/2021 | Millet |
| 11,202,769 B2 | 12/2021 | Millet |
| 11,241,403 B2 | 2/2022 | Millet |
| 11,690,817 B2 | 7/2023 | Millet |
| 2001/0014696 A1 | 8/2001 | Veech |
| 2001/0041736 A1 | 11/2001 | Veech |
| 2002/0013339 A1 | 1/2002 | Martin et al. |
| 2003/0022937 A1 | 1/2003 | Veech |
| 2004/0138293 A1 | 7/2004 | Werner et al. |
| 2004/0266872 A1 | 12/2004 | Veech |
| 2005/0129783 A1 | 6/2005 | Mccleary et al. |
| 2006/0165777 A1 | 7/2006 | Solomon et al. |
| 2006/0275253 A1 | 12/2006 | Ushida et al. |
| 2007/0029913 A1 | 2/2007 | Chen |
| 2007/0135376 A1 | 6/2007 | Henderson |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0131475 A1 | 5/2009 | Uesugi et al. |
| 2009/0253781 A1 | 10/2009 | Veech |
| 2009/0325984 A1 | 12/2009 | Costentin et al. |
| 2010/0041751 A1 | 2/2010 | Henderson |
| 2010/0056631 A1 | 3/2010 | Hisamura et al. |
| 2010/0197758 A1 | 8/2010 | Andrews et al. |
| 2010/0210726 A1 | 8/2010 | Kuriyama |
| 2010/0298294 A1 | 11/2010 | Clarke et al. |
| 2011/0237666 A1 | 9/2011 | Clarke et al. |
| 2011/0287114 A1 | 11/2011 | Johnson |
| 2012/0053240 A1 | 3/2012 | Rathmacher et al. |
| 2012/0071548 A1 | 3/2012 | Veech |
| 2012/0171165 A1 | 7/2012 | Buck et al. |
| 2012/0202891 A1 | 8/2012 | Stinchcomb et al. |
| 2013/0079406 A1 | 3/2013 | Veech |
| 2013/0337116 A1 | 12/2013 | Petralia |
| 2014/0256808 A1 | 9/2014 | Henderson |
| 2014/0350105 A1 | 11/2014 | D'Agostino et al. |
| 2015/0065571 A1 | 3/2015 | Clarke et al. |
| 2015/0132280 A1 | 5/2015 | Lopez et al. |
| 2015/0320809 A1 | 11/2015 | Carpenter et al. |
| 2016/0193173 A1 | 7/2016 | Clarke et al. |
| 2016/0256411 A1 | 9/2016 | Aung-Din |
| 2017/0020844 A1 | 1/2017 | Galinski |
| 2017/0029650 A1 | 2/2017 | Veling et al. |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | Dehaan et al. |
| 2018/0021274 A1 | 1/2018 | Arnold |
| 2018/0021281 A1 | 1/2018 | Berger |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2018/0214399 A1 | 8/2018 | Spector et al. |
| 2019/0099394 A1 | 4/2019 | Ari et al. |
| 2019/0151267 A1 | 5/2019 | Millet |
| 2019/0167613 A1 | 6/2019 | Millet |
| 2019/0167614 A1 | 6/2019 | Millet |
| 2019/0177673 A1 | 6/2019 | Llosa et al. |
| 2019/0183220 A1 | 6/2019 | Takada |
| 2019/0183820 A1 | 6/2019 | Millet |
| 2019/0183821 A1 | 6/2019 | Millet |
| 2019/0191755 A1 | 6/2019 | Garvey et al. |
| 2019/0209501 A1 | 7/2019 | Tinsley et al. |
| 2019/0262293 A1 | 8/2019 | Millet |
| 2019/0313682 A1 | 10/2019 | Nagel |
| 2019/0321309 A1 | 10/2019 | Millet |
| 2020/0078973 A1 | 3/2020 | Valeze et al. |
| 2020/0140371 A1 | 5/2020 | Verdin et al. |
| 2020/0253909 A1 | 8/2020 | Millet |
| 2020/0268701 A1 | 8/2020 | D'Agostino et al. |
| 2021/0205241 A1 | 7/2021 | Millet |
| 2023/0072854 A1 | 3/2023 | Purpura et al. |
| 2023/0115966 A1 | 4/2023 | Wells et al. |

FOREIGN PATENT DOCUMENTS

| | | |
|---|---|---|
| CN | 1347319 A | 5/2002 |
| CN | 1972698 A | 5/2007 |
| CN | 101674730 A | 3/2010 |
| CN | 101678043 A | 3/2010 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| CN | 109480284 A | 3/2019 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| FR | 2997302 A1 | 5/2014 |
| ID | 201701176 | 2/2017 |
| JP | 11-060434 A | 3/1999 |
| JP | 2002-521330 A | 7/2002 |
| JP | 2004-035417 A | 2/2004 |
| JP | 2015-042644 A | 3/2015 |
| JP | 2015-514104 A | 5/2015 |
| JP | 2016-514725 A | 5/2016 |
| JP | 2016-121128 A | 7/2016 |
| JP | 2017-046688 A | 3/2017 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2009/089144 A1 | 7/2009 |
| WO | 2010/021766 A1 | 2/2010 |
| WO | 2011/101171 A1 | 8/2011 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 2017/156446 A1 | 9/2017 |

(56) References Cited

FOREIGN PATENT DOCUMENTS

| | | |
|---|---|---|
| WO | 2017/165443 A1 | 9/2017 |
| WO | 2017/165445 A1 | 9/2017 |
| WO | 2017/208217 A2 | 12/2017 |
| WO | 2018/055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2018/187852 A1 | 10/2018 |
| WO | 2019/018683 A1 | 1/2019 |
| WO | 2019/108683 A1 | 6/2019 |
| WO | 2019/204148 A1 | 10/2019 |
| WO | 2019/237152 A1 | 12/2019 |

OTHER PUBLICATIONS

Sorensen et al. ("Simultaneous determination of β-hydroxybutyrate and β-hydroxy-β-methylbutyrate in human whole blood using hydrophilic interaction liquid chromatography electrospray tandem mass spectrometry", Clinical Biochemistry, 2013, vol. 46, pp. 1877-1883) (Year. 2013).

Anonymous: "Blue Lemon Ice Advanced Formula", MINTEL, Database accession No. 4315637, 2016, pp. 3.

Anonymous: "Strawberry Pineapple Flavour Pre-Exertion Performance Optimizer", MINTEL, Database accession No. 5661617, 2018, pp. 4.

Budin. N et al., "Efficient synthesis of the ketone body ester (R)-3-hydroxybutyryl-(R)-3-hydroxybutyrate and its (S,S) enantiomer," Bioorganic Chemistry, vol. 80, Oct. 2018, pp. 560-564.

Huang Dexiang, "Clinical Parenteral nutrition", Jan. 31, 1994, pp. 1-20.

Kaster M.P. et al., "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.

Lonza, Duocap Capsules, Feb. 16, 2018, https://web.archive.org/web/20180216001656/https://www.capsugel.com/consumer-health-nutrition-products/duocap-capsules (Year: 2018).

Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.

Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.

Mangels D.R. et al, "Catechins as Potential Mediators of Cardiovascular Health", Translational Sciences, vol. 37, No. 5, May 1, 2017, pp. 757-763.

A New Toy Measuring Blood Ketones. Diet Doctor, Aug. 21, 2012. Dowloaded Apr. 1, 2015. http://www.dietdoctor.com/a-new-toy-measuring-blood-ketoones.

Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.

Arendash et al. "Caffeine and Coffee as Therapeutics Against Alzheimer's Disease", Journal of Alzheimer's Disease 20, 2010, S117-S126.

Bastin et al., "Salt Slection and Optimisation Procedures for Pharmaceutical New Chemical Entities", American Chemical Society and The Royal Society of Chemistry, vol. 4, No. 5, 2000, pp. 427-435.

Blazquez et al. Journal of Neurochemistry, 1999, vol. 72 No. 4, pp. 1759-1768. (Year: 1999).

Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.

Craciun, S. et al. Microbial conversion of choline to trimethylamine requires a glycyl radical enzyme, 2012, PNAS, 109(52): 21307-21312 (Year: 2012).

Dietary Guidelines Recommendations at https://health.gov/our-work/food-nutrition/2015-2020-dietary-guidelines/guidelines/appendix-7/ (2010) (retrieved from the internet Oct. 20, 2020) (Year: 2010).

Extended European Search Report issued in PCT/US2017021886 dated Oct. 17, 2019.

Extended European Search Report received for EP Patent Application No. 19788264.0, dated Dec. 20, 2021, 11 pages.

First Examination Report for New Zealand Patent Application No. 711433 issued by the New Zealand Intellectual Property Office dated Mar. 10, 2016.

First Office Action issued by the Chinese State Intellectual Property Office dated Nov. 4, 2016 for corresponding Chinese Patent Application No. 201480016818.0.

Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.

Hashim, Sami A., et al., "Ketone body therapy: from the ketogenic diet to the oral administration of ketone ester", Journal of Lipid Research, vol. 55, 2014.

Haywood A, Glass BD. Pharmaceutical excipient—where do we begin? Australian Prescriber. 2011; 34: 112-114.

Henderson, Samuel T. "Ketone Bodies as a Therapeutic for Alzheimer's Disease." Neurotherapeutics. Jul. 2008;5(3):470-80.

Holtzman et al., "Role of adenosine receptors in caffeine tolerance", J. Pharmacol. Exp. Ther., 1991 ;256(1 ):62-68.

International Preliminary Report on Patentability received for PCT Patent Application No. PCT/US2020/016952, dated Aug. 26, 2021, 7 pages.

International Preliminary Report on Patentability received for PCT Patent Application No. PCT/US20/37289, dated Dec. 30, 2021, 6 pages.

International Preliminary Report on Patentability received for PCT Patent Application No. PCT/US2019/048364, dated Mar. 11, 2021, 7 pages.

International Preliminary Report on Patentability received for PCT Patent Application No. PCT/US2020/017552, dated Aug. 26, 2021, 7 pages.

International Preliminary Report on Patentability received for PCT Patent Application No. PCT/US2020/017555, dated Aug. 26, 2021, 7 pages.

International Preliminary Report on Patentability received for PCT Patent Application No. PCT/US2020/017556, dated Aug. 26, 2021, 7 pages.

International Preliminary Report on Patentability received for PCT Patent Application No. PCT/US2020/033159, dated Nov. 25, 2021, 6 pages.

International Search Report and Written Opinion issued in PCT/US19/48357 dated Nov. 18, 2019.

International Search Report and Written Opinion issued in PCT/US19/48364 dated Nov. 15, 2019.

International Search Report and Written Opinion issued in PCT/US20/16952 dated Apr. 22, 2020.

International Search Report and Written Opinion issued in PCT/US20/17552 dated May 4, 2020.

International Search Report and Written Opinion issued in PCT/US20/17555 dated May 4, 2020.

International Search Report and Written Opinion issued in PCT/US20/17556 dated May 4, 2020.

International Search Report and Written Opinion received for PCT Patent Application No. PCT/US20/017555, dated May 4, 2020, 8 pages.

International Search Report and Written Opinion received for PCT Patent Application No. PCT/US2020/033159, dated Aug. 12, 2020, 9 pages.

(56) References Cited

OTHER PUBLICATIONS

International Search Report and Written Opinion received for PCT Patent Application No. PCT/US21/045186, dated Nov. 22, 2021, 10 pages.
International Search Report cited in PCT/US19/27214 dated Jun. 25, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
Karppanen et al., J. Human Hypertension (2005), vol. 19, pp. S10-S19. (Year: 2005).
Kesl, et al., "Effects of exogenous ketone supplementation on blood ketone, glucose, triglyceride, and lipoprotein levels in Sprague-Dawley rats", Nutrition & Metabolism (2016).
Kim Do Young et al., "Ketone bodies are protective against oxidative stress in neocortical neurons," Journal of Neurochemistry, vol. 101, Issue 5, Jun. 1, 2007, pp. 1316-1326.
Kirsch, Jr et al. "Butanediol Induced Ketosis Increases Tolerance to Hypoxia in the Mouse." Stroke. 1980, vol. 11, No. 3, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, "Value of VLCD Supplementation with Medium Chain Triglycerides", Int J Obes Relat Metab Disord, Sep. 2001, 25(9), pp. 1393-1400.
Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Murray, Andrew J., et al. "Novel ketone diet enhances physical and cognitive performance", The FASEB Journal, Vo. 30 Dec. 2016.
Nova Max Plus Glucose and Ketone Testing with One Monitor. Downloaded Apr. 1, 2015. http://www.novacares.com/nova-max-plus/.
PCT International Search Report and Written Opinion cited in PCT/US2014/031237 dated Jul. 15, 2014.
Pete J Cox et al., "Acute nutritional ketosis: implications for exercise performance and metabolism", Extreme Physiology & Medicine, vol. 3, Issue 1, Dec. 1, 2014, pp. 1-9.
A New Toy Measuring Blood Ketones. Diet Doctor, Aug. 21, 2012. Downloaded Apr. 1, 2015. http://www.dietdoctor.com/a-new-toy-measuring-blood-ketoones.
Arnold, Instant Ketosis?, (2013), Aug. 4, 2013 (retrieved on Apr. 21, 2017), p. 1-3. Retrieved from the internet; URL: < http://patrickamoldblog.com/instant-ketosis/. (Year: 2013).
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Dolson, Laura. How to Test Your Blood for Ketones. Downloaded Apr. 1, 2015. http://lowcarbdiets.about.eom/od/KetogenicDiets/a/How-to-Test-Blood-For-Ketones.htm.
Hashim, Sarni A., et al., "Ketone body therapy: from the ketogenic diet to the oral administration of ketone ester", Journal of Lipid Research, vol. 55, 2014.
Haywood A, Glass BD. Pharmaceutical excipients—where do we begin? Australian Prescriber. 2011; 34: 112-114.
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).

International Search Report and Written Opinion received for PCT Patent Application No. PCT/US20/37289, dated Sep. 30, 2020, 8 pages.
International Search Report and Written Opinion received for PCT Patent Application No. PCT/US21/17078, dated Apr. 23, 2021, 9 pages.
International Search Report cited in PCT/US18/62093 dated Feb. 1, 2019.
Kesl, et al., "Effects of exogenous ketone supplementation on blood ketone, glucose, triglyceride, and lipoprotein levels in Spraque-Dawley rats", Nutrition & Metabolism (2016).
Kirsch, Jr et al. "Butanediol Induced Ketosis Increases Tolerance to Hypoxia in the Mouse." Stroke. 1980. vol. 11, No. 5, pp. 506-513.
Malo, M. S. et al., Intestinal alkaline phosphatase preserves the normal homeostasis of gut microbiota, 2010, Gut, 59, 1476-1484 (Year: 2010).
Murray, Andrew J., et al. "Novel ketone diet enhances physical and cognitive performance", The FASEB Journal, No. 30 Dec. 2016.
Optical Purity and Enantiomeric Excess at https://www.masterorganicchemistry.com/2017/02/24/optical-purity-and-enantiomeric-excess/. (Retrieved from the internet Nov. 6, 2018) (Year: 2018).
PCT International Search Report and Written Opinion issued by the International Searching Authority dated Jul. 15, 2014 or International Patent Application No. PCT/US2014/031237.
Pubchem, "Acetoacetic acid" Electronic Resource: https://pubchem.ncbi.nim.nih.gov/compound/Acetoacetic-acid, Retrieved on Sep. 3, 2019.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Shigeno et al. in Biosci. Biotech. Biochem., 56(2), 320-323 (1992) (Year: 1992).
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Robson et al. Expert Opin. Drug Saf. (2011), vol. 10, pp. 675-685 (Year: 2011).
Sajewicz et al. in Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Stubbs et al., "On the Metabolism of Exogenous Ketones in Humans", frontiers in Physiology, vol. 8, 2017, 13 pages.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Tsai et al., "Stereoselective effects of 3-hydroxybutyrate on glucose utilization of rat cardiomyocytes" life Sciences 78(2006) pp. 1385-1391.
Vandenberghe et al. in Can. J. Physiol. Pharmacol. 95: 455-458 (2017) (Published at www.nrcresearchpress.com/cjpp on Nov. 25, 2016). (Year: 2016).
Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.

(56) References Cited

OTHER PUBLICATIONS

Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.
Written Opinion cited in PCT/US19/27214 dated Jun. 25, 2019.
3-Hydroxybutyric acid; PubChem, 2023 (Year: 2023).
Bala et al. Drug Invention Today. Jun. 1, 2018;10(6), 929-931.
Daniells, Stephen, 'This is caffeine-evolved': Ingenious Ingredients co-founder talks up potential of paraxanthine, Nov. 3, 2021, 2 pages, retrieved from https://www.nutraingredients-usa.com/Article/2021/11/03/This-is-caffeine-evolved-Ingenious-Ingredients-co-founder-talks-up-potential-of-paraxanthine accessed Feb. 7, 2023.
International Preliminary Report on Patentability received for PCT Patent Application No. PCT/US2021/063559, dated Jul. 6, 2023, 6 pages.
Paraxanthine—Pubchem—2023 (Year: 2023).
Sorensen et al. ("Simultaneous determination of B-hydroxybutyrate and B-hydroxy-B-methylbutyrate in human whole blood using hydrophilic interaction liquid chromatography electrospray tandem mass spectrometry", Clinical Biochemistry, 2013, vol. 46, pp. 1877-1883) (Year: 2013).
European Search Report received for EP Patent Application No. 20755289.4, mailed on Oct. 11, 2022, 7 pages.
European Search Report received for EP Patent Application No. 20755994.9, mailed on Sep. 21, 2022, 6 pages.
European Search Report received for EP Patent Application No. 20805593.9, mailed on Dec. 16, 2022, 9 pages.
Extended European Search Report received for EP Patent Application No. 20755770.3, mailed on Sep. 1, 2022, 7 pages.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Holscher, H. Dietary fiber and prebiotics and the gastrointestinal microbiota, 2017, Gut Microbes, 8(2): 172-184 (Year: 2017).
International Preliminary Report on Patentability received for PCT Patent Application No. PCT/US2021/017078, mailed on Aug. 18, 2022, 7 pages.
International Search Report and Written Opinion received for PCT Patent Application No. PCT/US2021/063559, mailed on Mar. 18, 2022, 9 pages.
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Lile et al. Drug Alcohol Depend. 2012, 122 (1-2), 61-69.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
National Center for Biotechnology Information. PubChem Compound Summary for CID 441, 3-Hydroxybutyric acid, https://pubchem.ncbi.nlm.nih.gov/compound/3-Hydroxybutyric-acid. (Year. 2005).
Parker, Steve, "Ketogenic Mediterranean Diet: Version 2.3," Nov. 23, 2010, pp. 1-3. (Year: 2010).
Rich A.J., "Ketone Bodies as Substrates," Proceedings of the Nutrition Society (1990), vol. 49, 361-373.
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Slavin, J. Fiber and Prebiotics: Mechanisms and Health Benefits, 2013, Nutrients, 5: 1417-1425 (Year: 2013).
The Medical Republic, 2018, Sustained Release Sodium Butyrate Supplement Now Available to Support Management of GI Disorders, https://medicalrepublic.com.au/sustained-release-sodium-butyrate-supplement-now-available-support-management-gi-disorders/15791; newly cited (Year: 2018).
Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).
Wu et al., "Medium-Chain Triglycerides in Infant Formulas and Their Relation to Plasma Ketone Body Concentrations," Pediatric Research, vol. 20, No. 4, (1986), pp. 338-341.
Yang Y. et al., Role of Adherent-Invasive *Escherichia coli* in Inflammatory Bowel Disease, Letters in Biotechnology , No. 06, Nov. 30, 2016.
Zaleski, A. et al., Butyric acid in irritable bowel syndrome, 2013, Prz Gastroenterol, 8(6), 350-353 (Year: 2013).
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
International Preliminary Report on Patentability received for PCT Patent Application No. PCT/US2014/031237, mailed on Oct. 1, 2015, 8 pages.
International Preliminary Report on Patentability received for PCT Patent Application No. PCT/US2017/021886, mailed on Sep. 20, 2018, 9 pages.
International Preliminary Report on Patentability received for PCT Patent Application No. PCT/US2018/062096, mailed on Jul. 2, 2020, 8 pages.
International Preliminary Report on Patentability received for PCT Patent Application No. PCT/US2019/027214, mailed on Oct. 29, 2020, 09 pages.
International Preliminary Report on Patentability received for PCT Patent Application No. PCT/US2019/048357, mailed on Mar. 11, 2021, 08 pages.
International Search Report and Written Opinion received for PCT Patent Application No. PCT/US2014/031237, mailed on Jul. 15, 2014, 11 pages.
International Search Report and Written Opinion received for PCT Patent Application No. PCT/US2017/021886, mailed on Jun. 1, 2017, 15 pages.
International Search Report and Written Opinion received for PCT Patent Application No. PCT/US2018/062096, mailed on Feb. 11, 2019, 13 pages.
International Search Report and Written Opinion received for PCT Patent Application No. PCT/US2019/027214, mailed on Jun. 25, 2019, 14 pages.
International Search Report and Written Opinion received for PCT Patent Application No. PCT/US2019/048357, mailed on Nov. 18, 2019, 13 pages.
International Search Report and Written Opinion received for PCT Patent Application No. PCT/US2020/016952, mailed on Apr. 22, 2020, 9 pages.
International Search Report and Written Opinion received for PCT Patent Application No. PCT/US2020/017552, mailed on May 4, 2020, 9 pages.
International Search Report and Written Opinion received for PCT Patent Application No. PCT/US2020/017556, mailed on May 4, 2020, 12 pages.
Lang Chaochun, "Healthy fitness and exercise prescription", Nov. 30, 2013, p. 201.
Yang Yue et al., "Research on sarcopenic obesity", Chinese Journal of Modern Medicine, vol. 20, No. 3, Mar. 25, 2018, pp. 98-101.
Yang Zeyi, "Biochemistry of sports nutrition scientific research progress", Mar. 31, 2004, vol. 23, No. 2, pp. 158-165.
Zeng Jing et al., "B-hydroxy-3-methyl- The clinical effects and mechanism", vol. 2, No. 2, Jun. 9, 2015, pp. 57-62.
Database GNPD Mintel, Sep. 29, 2016, anonymous, "Blue Lemon Ice Advanced Formula", XP093048090, Database accession No. 4315637, pp. 3.
European Search Report received for EP Patent Application No. 21750261.6, mailed on Feb. 2, 2024, 10 pages.
Office Action received for European Patent Application No. 20805593.9, mailed on Dec. 22, 2023, 7 pages.

(56) References Cited

OTHER PUBLICATIONS

Short, Jay, Effects of A Ketone/Caffeine Supplement On Cycling and Cognitive Performance, Master's thesis, Ohio State University, 61 pages, (Jan. 1, 2017).†

Sara, How do you know which product is right for you? How to choose exogenous ketones, https://ketosupplements.co.uk/how-to-choose-exogenous-ketones/, 10 pages, (Sep. 25, 2017).†

O'Meara, Cyndi, Changing Habits, Ketosis—Can we achieve it in a pill?, https://changinghabits.com.au/ketosis-can-we-achieve-it-in-a-pill/, 12 pages, (Jan. 13, 2017).†

\* cited by examiner
† cited by third party

NON-VASOCONSTRICTING ENERGY-PROMOTING COMPOSITIONS CONTAINING KETONE BODIES

CROSS-REFERENCE TO RELATED APPLICATIONS

This application in a continuation-in-part of U.S. patent application Ser. No. 16/849,901, filed Apr. 15, 2020, which claims the benefit of U.S. Provisional Application No. 62/864,989, filed Jun. 21, 2019, which are incorporated herein by reference in their entirety

BACKGROUND

Energy drinks are beverages used by consumers to promote wakefulness, maintain alertness, and enhance mood and cognition. Typical gas station energy drinks include common ingredients such as caffeine and sugar. Some may also include vitamins, electrolytes, or amino acids.

Despite widespread use, there are several health concerns surrounding consumption of gas station energy drinks, particularly surrounding their effects on the cardiovascular system. Such energy drinks have been shown to increase heart rate, increase blood pressure, and even thicken the blood. Energy drinks may also affect the brain in undesirable ways, such as by raising stress levels and inducing anxiety, insomnia, gastrointestinal irritation, muscle twitching, and periods of prolonged restlessness.

Energy drinks are also associated with high levels of fatigue, irritability, and sub-optimal cognition following the initial boost after consumption. This energy "crash" can be long lasting and unpleasant. As the stimulating effects wear off, levels of adrenaline, dopamine, and acetylcholine begin to drop, and blood sugar levels may swing erratically, often leaving the user feeling more fatigued, irritable, and unfocused than before consuming the energy drink. In the case of caffeine in particular, the user's adenosine levels may continue to rise after dosing. When caffeine is no longer available to block adenosine receptors, the rapid flood of built-up adenosine to the receptors can contribute to the perceived crash.

To date, popular gas station energy drinks have generally failed to improve the overall quality of life and well-being of users. Rather, such energy drinks provide a short-lived boost in desired alertness but with a subsequent crash that often tends to be so uncomfortable as to negate the benefits and place consumption of energy drinks as a net negative experience. When used to stay awake while driving, gas station energy drinks can cause high levels of stress and possibly contribute to "road rage". For long haul drives, the mental and/or physical "crash" by the user is potentially harmful or even fatal if it leads to a highway crash.

Accordingly, there is an ongoing need for compositions that are capable of promoting a natural and sustained feeling of wakefulness, maintaining a natural feeling of alertness without jitteriness, increasing concentration, enhancing mood, and/or enhancing cognition without the typical energy crash and without damaging the long-term physiological or mental health of the user.

SUMMARY

Disclosed herein are energy-promoting compositions formulated to provide rapid and effective onset of physical and mental energy, while minimizing or avoiding typical crash effects that plague conventional energy-promoting products, particularly gas station energy drinks advertised on billboards, radio, and television. In one embodiment, the energy-promoting composition is formulated as a liquid energy drink. Other embodiments may include other dosage forms.

In one embodiment, the energy-promoting composition comprises: (i) a caloric energy source comprising an exogenous ketone body component; (ii) a vasodilator component; and (iii) a stimulant component that increases alertness. The energy-promoting composition may further optionally comprise (iv) a nootropic component, such as a dopamine and/or acetylcholine promoter. In most if not all cases, the vasodilator, stimulant, and nootropic components do not provide caloric energy.

The main, if not exclusive, caloric energy source comprises an exogenous ketone body component, such as beta-hydroxybutyrate and/or acetoacetate. The ketone body component may be provided as a salt, ester, free acid (i.e., beta-hydroxybutyric acid, acetoacetic acid), or combination thereof. It may also include a ketone body precursor, such as 1,3-butanediol or ester thereof.

The vasodilator component may comprise one or more of quercetin, L-citrulline and/or salt thereof, L-arginine and/or salt thereof, agmatine and/or salt thereof, nitrates, gallic acid, coenzyme Q10 (CoQ10), trimethylglycine, niacin, theanine, theobromine, garlic, magnesium, grape seed extract, green tea extract, catechins and/or epicatechins (e.g., Vaso 6), cacao, proanthocyanidins, galloylated proanthocyanidins, L-norvaline, beta-alanine, glutathione, and taurine. In some embodiments, the vasodilator component is a (-)-epicatechin such as epicatechin-(4-8)-epicatechin-(4-8)-epicatechin or epicatechin-(4-8)-epicatechin-(4-8)-epicatechingallate.

The stimulant component may comprise at least one of caffeine, methylliberine, or theacrine. The stimulant component may additionally or alternatively include other stimulant compounds that increase alertness but provide no caloric energy described herein, such as one or more other adenosine receptor antagonists, other phosphodiesterase inhibitors, epinephrine and/or norepinephrine promoters or combinations thereof. Caffeine is a preferred stimulant component because it is widely utilized, well understood, well tolerated, easy to dose, and familiar to almost all users. Caffeine may assist the body in metabolizing available sources of caloric energy but is not itself a source of caloric energy. Methylliberine is an effective short-term stimulant. Theacrine is an effective long-term stimulant.

The individual components of the energy-promoting composition beneficially and synergistically interact together to enhance the overall energy-promoting effect of the composition and provide a more natural feeling energy boosting effect compared to popular gas station energy drinks. The combination of an exogenous ketone body component, vasodilator component, and stimulant component in a single formulation provides benefits not obtainable from a composition that includes only one or two of the components.

The caloric energy provided by the ketone body component attenuates the crash effect of the stimulant component by beneficially smoothing out and/or prolonging the experienced energy levels of the user. For example, the ketone body component provides a stable caloric energy source that avoids or minimizes the blood sugar swings and/or insulin spikes and/or mood swings commonly associated with conventional energy drinks containing a sugar component.

The vasodilator component beneficially counteracts the vasoconstriction of the stimulant component and also functions to improve the pharmacokinetic distribution of the other components. In other words, the vasodilator component functions to increase blood flow to peripheral tissues of the body so that the ketone bodies and the stimulant compound(s) can more effectively move from the digestive system to their intended targets (e.g., brain and muscle tissues).

The stimulant component beneficially interacts with the ketone body component by enhancing pharmacokinetic absorption and uptake of the ketone bodies into the tissues so it can be readily utilized as an energy source. In other words, the stimulant component, while providing no caloric energy, has been found to increase the efficiency in which the ketone body component is actually taken into cells and metabolized as caloric energy.

It is to be understood that both the foregoing general description and the following detailed description are exemplary and explanatory only and are not restrictive of the embodiments claimed.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification wherein like reference numerals designate corresponding parts in the various figures and wherein the various elements depicted are not necessarily drawn to scale; and wherein:

DETAILED DESCRIPTION

I. Definitions

Figure 1:
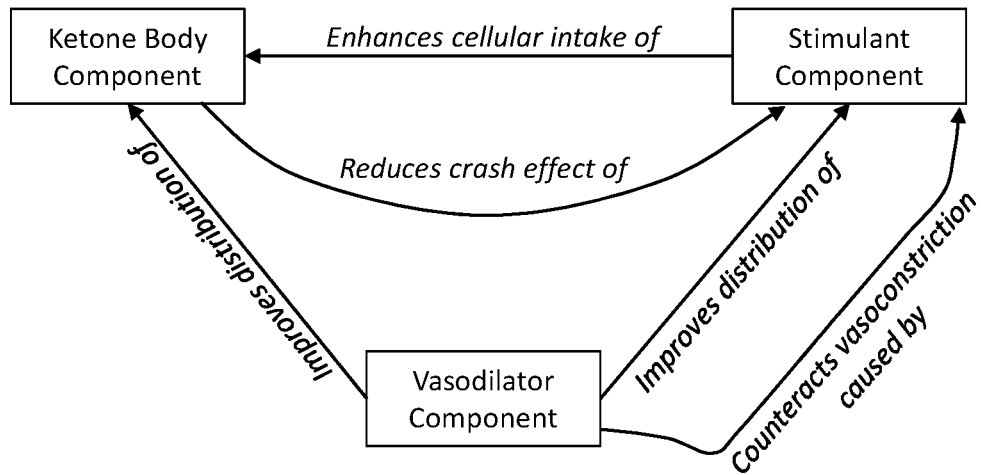
FIG. 1 is a flow diagram that schematically illustrates the multiple interactions between the individual ketone body, vasodilator, and stimulant components of an energy-promoting composition.

As used herein, the term "crash" or "crash effect" refers to the state a user may experience following consumption of a stimulant such as caffeine that increases alertness but provides no source of caloric energy. A crash is characterized by unpleasant effects such as extreme tiredness, difficulty concentrating, irritability, diminished judgment, and/or poor mood. As the stimulant wears off, neurotransmitter and/or hormone (e.g., dopamine, acetylcholine, adrenaline) levels may drop relatively sharply, and blood sugar level swings may become larger than normal. Insulin spikes may also exacerbate the crash. In the case of caffeine in particular, adenosine levels may continue to rise after dosing. When caffeine is no longer available to block adenosine receptors, the rapid flood of built-up adenosine to the receptors can contribute to the crash.

As used herein, the term "energy level," "experienced energy level," or "subjective energy level" refers to the level of wakefulness and/or focus experienced by the user. They can be both mental and physical in nature. While these may be relatively subjective properties, they are readily understood by users and are amenable to measurement through appropriate questioning and/or surveying. For example, as with various clinical mood or pain rating measurements, a user may describe energy level on a scale (e.g., 1 to 10 or 1 to 100). Other objective measures of wakefulness are also known in the art, such as those described in Michael et al. (2008) "Effects of caffeine on alertness as measured by infrared reflectance oculography" Psychopharmacology, 200: 255-260. Although caffeine may increase alertness and metabolism of available caloric energy sources such as fats and sugars, it is not itself a source of caloric energy, i.e., energy consumed by cells to produce ATP. The ketone body component is the primary, if not sole, caloric energy source in the disclosed compositions.

The term "administration" or "administering" is used herein to describe the process in which an energy-promoting composition is taken by or delivered to a subject. The composition may be administered in various ways including orally, rectally, or intragastrically, among others, though typical embodiments will be formulated for oral administration.

The term "dosage form" refers to the structural form the composition is provided in and/or the vehicle by which the energy-promoting composition is delivered to the user. Example dosage forms include, but are not limited to, tablets, capsules, powders, gels, food products, food additives, beverages/drinks (e.g., in cans, bottles, cartons, pouches, squeeze containers, and the like), beverage additives, candies (e.g., suckers, gummies, pastilles), food supplements, sprays, injectables, and suppositories. Preferred embodiments are formulated as liquids for oral consumption.

The term "unit dose" refers to a dosage form that is configured to deliver a specified quantity or dose of composition or component thereof. Dosage forms may be configured to provide a full unit dose or fraction thereof (e.g., ½, ⅓, or ¼ of a unit dose).

Another dosage form that can be used to provide a unit dose of composition or component thereof is a "unit dose measuring device", such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). An example use of such measuring device(s) is in kit together with a bulk container.

For example, a "bulk container", such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A "kit" for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers. A bulk container may contain liquid or solid forms of composition.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as cups, scoops, syringes, droppers, spoons, spatulas, ladles, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

The term "exogenous ketone body" refers to beta-hydroxybutyrate, acetoacetate, or a combination thereof. These compounds may be utilized by a subject's body as a caloric energy source when supplemented in a usable form. Where beta-hydroxybutyrate is included, it may be provided as purified or enriched with the R enantiomer, as purified or enriched with the S enantiomer, or as a racemic mixture. The exogenous ketone bodies may be provided in a free acid form (i.e., beta-hydroxybutyrate and/or acetoacetic acid), salt form, ester form, or combination thereof. Ketone body precursors, such as 1,3-butanediol or ester thereof can be included.

II. Energy-Promoting Compositions

In one embodiment, an energy-promoting composition comprises: (i) a caloric energy source comprising an exogenous ketone body component; (ii) a vasodilator component; and (iii) a stimulant component that increases alertness. The energy-promoting composition may further optionally comprise (iv) a nootropic component such as a dopamine and/or acetylcholine promoter. In most if not all cases, the vasodilator, stimulant, and nootropic components do not provide caloric energy.

A. Ketone Bodies

The caloric energy source in the energy-promoting compositions is the heart of the invention in comparison to which the other components are attenuated The prime or sole caloric energy source used as fuel by the body's cells comprises an exogenous ketone body component such as beta-hydroxybutyrate and/or acetoacetate. The ketone body component may be provided as a salt, ester, free acid (i.e., beta-hydroxybutyric acid, acetoacetic acid), or combination thereof. A ketone body precursor such as 1,3-butanediol or ester thereof may optionally be included. Exogenous ketone bodies are particularly beneficial for supporting stable energy levels without excessive "jitters" and without a rapid crash following consumption. The brain can utilize ketone bodies as a caloric energy source, and in many instances, ketone bodies are the preferred source of caloric energy for brain cells. An increase in the proportion of the brain's caloric energy demand met by ketone bodies, as opposed to glucose, beneficially provides a stable and relatively long-lasting caloric energy source to fuel the brain. Ketone bodies can provide an elevated caloric fuel source without causing an insulin spike, as is common with rapid consumption of sugars.

"Beta-hydroxybutyrate," also known as β-hydroxybutyrate, 3-hydroxybutyrate, βHB, or BHB, is the deprotonated form of beta-hydroxybutyric acid, a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

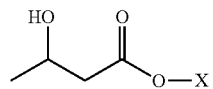

where X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

"Acetoacetate" is the deprotonated form of acetoacetic acid, which is a keto carboxylic acid having the formula $CH_3COCH_2COOH$. The deprotonated form present at typical biological pH levels is $CH_3COCH_2COO^-$. The general chemical structure shown below represents acetoacetate compounds that may be utilized in the disclosed compositions:

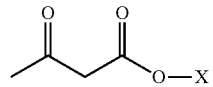

where X can be hydrogen, metal ion, amino cation, such as from an amino acid, alkyl, alkenyl, aryl, or acyl.

When X is a hydrogen, the compound is acetoacetic acid. When X is a metal ion or an amino cation, the compounds is an acetoacetate salt. When X is alkyl, alkenyl, aryl, or acyl, the compounds is an acetoacetate ester. The foregoing compounds can be in any desired physical form, such as crystalline, powder, solid, liquid, solution, suspension, or gel.

The beta-hydroxybutyrate and acetoacetate compounds described above may be collectively referred to herein as "ketone bodies," "exogenous ketone bodies," a "ketone body component," or "exogenous ketones."

The term "beta-hydroxybutyrate mixed salt-acid composition" means a composition that includes one or more salts of beta-hydroxybutyrate and free beta-hydroxybutyric acid.

Similarly, the term "acetoacetate mixed salt-acid composition" means a composition that includes one or more salts of acetoacetate and free acetoacetic acid.

The terms "beta-hydroxybutyrate salt" and "acetoacetate salt" do not mean or imply any particular physical state, such as a crystalline, powder, other solid form, dissolved in water to form a liquid solution, dispersed in a liquid to form a suspension, or a gel. A salt can be formed in solution by neutralizing beta-hydroxybutyric acid and/or acetoacetic acid with a strong or weak base, such as an alkali or alkaline earth metal hydroxide, carbonate, or bicarbonate, basic amino acid, and the like.

The term "free beta-hydroxybutyric acid" means the sum of non-deprotonated and deprotonated beta-hydroxybutyric acid molecules. A deprotonated beta-hydroxybutyric acid molecule generally means a molecule that has released a proton to form a hydronium ion ($H_3O+$) and a beta-hydroxybutyrate anion (e.g., dissolved in water).

Similarly, the term "free acetoacetic acid" means the sum of non-deprotonated and deprotonated acetoacetic acid molecules. A deprotonated acetoacetic acid molecule generally means a molecule that has released a proton to form a hydronium ion ($H_3O+$) and an acetoacetate anion (e.g., dissolved in water).

Free beta-hydroxybutyric acid molecules are typically not deprotonated to any significant degree when contained in a beta-hydroxybutyrate mixed salt-acid composition in dry powder or other solid form. In such cases, the fractional amount of free beta-hydroxybutyric acid in a beta-hydroxybutyrate mixed salt-acid composition on a weight basis is the weight of free beta-hydroxybutyric acid divided by the combined weight of free beta-hydroxybutyric acid and beta-hydroxybutyrate salt(s). On a molar basis, the fractional amount of free beta-hydroxybutyric acid in an beta-hydroxybutyrate mixed salt-acid composition are the molar equivalents of free beta-hydroxybutyric acid divided by the sum of molar equivalents of free beta-hydroxybutyric acid and beta-hydroxybutyrate anions provided by the beta-hydroxybutyrate salt(s). Similar principles apply to acetoacetic acid.

When dissolved in water, a portion of the beta-hydroxybutyric acid will typically dissociate into beta-hydroxybutyrate anions and hydronium ions ($H_3O+$). As a result, beta-hydroxybutyric acid molecules can exchange protons and cations with dissolved beta-hydroxybutyrate salts. For purposes of defining the relative amounts of beta-hydroxybutyric acid and beta-hydroxybutyrate salt(s) in a beta-hydroxybutyrate mixed salt-acid composition, dissociation of beta-hydroxybutyric acid molecules and the exchange of protons and cations is not understood as changing the molar ratio of free beta-hydroxybutyric acid relative to beta-hydroxybutyrate anions from the beta-hydroxybutyrate salt(s). The total quantity of free beta-hydroxybutyric acid molecules in solution is the sum of dissolved beta-hydroxybutyric acid molecules that are not deprotonated and beta-hydroxybutyrate anions formed by deprotonation of beta-hydroxybutyric acid molecules. Similar principles apply to acetoacetic acid.

Stated another way, the total molar equivalents of beta-hydroxybutyric acid in solution, whether or not deprotonated, is understood to be the difference between (i) the sum of molar equivalents of non-deprotonated beta-hydroxybutyric acid molecules and total molar equivalents of beta-hydroxybutyrate anions in solution (from all sources) and (ii) the total molar equivalents of cationic charge provided by cations from the beta-hydroxybutyrate salt compounds (which equals the total molar equivalents of beta-hydroxybutyrate anions provided by the beta-hydroxybutyrate salt(s)). Alkali metal cations such as sodium and potassium provide 1 mole of cationic charge per mole of metal cations. Alkaline earth metal cations such as magnesium and calcium, on the other hand, provide 2 moles of cationic charge per mole of metal cations. 1 mole of deprotonated beta-hydroxybutyric acid molecules provide 1 mole of anionic charge and one mole of cationic charge. Similar principles apply to acetoacetic acid.

In view of the foregoing, the molar fraction of beta-hydroxybutyric acid in solution in relation to total moles of beta-hydroxybutyrate molecules from the beta-hydroxybutyrate mixed salt-acid composition in solution is [(i)−(ii)]÷(i), and the molar fraction of beta-hydroxybutyrate molecules from the beta-hydroxybutyrate salt(s)) in solution is (ii)÷(i). Multiplying the molar fraction of each by 100 gives the percentage of each in solution. Similar principles apply to acetoacetate mixed salt-acid compositions.

By way of example, if 100 molar equivalents of beta-hydroxybutyrate mixed salt-acid composition in a dry powdered state contained 5% of free non-deprotonated beta-hydroxybutyric acid and 95% beta-hydroxybutyrate salt(s) on a molar basis, there would be essentially 5 molar equivalents of beta-hydroxybutyric acid molecules and 95 molar equivalents of beta-hydroxybutyrate anions. When there is sufficient water to dissolve the beta-hydroxybutyrate salt(s), and if a portion of the beta-hydroxybutyric acid molecules were deprotonated, the molar equivalents of non-deprotonated beta-hydroxybutyric acid would be less than 5 and the molar equivalents of beta-hydroxybutyrate anions would be greater than 95. The extent of deprotonation of beta-hydroxybutyric acid in solution is related to solution pH. Similar principles apply to acetoacetate mixed salt-acid compositions.

Beta-hydroxybutyrate mixed salt-acid compositions, when used, contain one or more beta-hydroxybutyrate salts and beta-hydroxybutyric acid. Providing a quantity of beta-hydroxybutyric acid is beneficial because of its much quicker absorption response time compared to salt forms of beta-hydroxybutyrate. Moreover, even though free beta-hydroxybutyric acid is ordinarily a liquid that forms an acidic solution of low pH when mixed in water and has an unpalatable taste, when combined with salt forms of beta-hydroxybutyrate and where the amount of beta-hydroxybutyric acid is relatively small relative to the salt form(s), the composition can still form a solid, powder or other form typical of salt forms. In such case, the combined salt and acid forms of BHB have acceptable pH and taste. beta-hydroxybutyrate mixed salt-acid compositions have substantial advantages over pure beta-hydroxybutyrate salts, including increased absorption rate, increased bioavailability, lower electrolyte load, ease of manufacture, significantly improved taste, and reduced need for citric acid or other edible acids to obtain a composition with neutral or acidic pH (e.g., compositions made acidic to preserve and prevent the compositions from supporting microbial growth). Similar principles apply to acetoacetate mixed salt-acid compositions.

In some embodiments, the beta-hydroxybutyrate mixed salt-acid composition contains less than 100% of one or more beta-hydroxybutyrate salts and greater than 0% of free beta-hydroxybutyric acid. Beta-hydroxybutyrate mixed salt-acid compositions may contain, on a molar basis, up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, of one or more beta-hydroxybutyrate salts and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, of free beta-hydroxybutyric acid. The foregoing percentages are expressed on a molar basis (e.g., moles of beta-hydroxybutyric acid relative to total moles of beta-hydroxybutyrate compounds in both salt and acid forms). Similar principles apply to acetoacetate mixed salt-acid compositions and percentages.

The ketone body component may be included in an amount ranging from about 0.5 g to about 20 g, or about 1 g to about 15 g, or about 2 g to about 10 g, or about 3 g to about 8 g. The ketone body component is preferably comprised of a beta-hydroxybutyrate mixed acid-salt composition, such as a mixture of beta-hydroxybutyrate salt(s) and beta-hydroxybutyric acid, preferably including a mixture of beta-hydroxybutyrate salt(s), though ketone body forms may be additionally or alternatively included, as mentioned above, such as acetoacetate compounds.

When a salt mixture is utilized in the ketone body component, it is preferred that the salt mixture limit the amount of sodium ions to avoid exacerbating or causing high blood pressure or other electrolyte imbalance. As explained above, the stimulant component is already associated with causing increased blood pressure. Although the vasodilator component beneficially counteracts at least some of these effects, excessive sodium ions in the blood may undo the benefits of the vasodilator component and/or promote other negative health effects related to electrolyte imbalances and particularly sodium/potassium imbalances. In some embodiments, the total amount of sodium provided by a daily dose of the energy-promoting composition does not exceed four times the recommended daily allowance (RDA) for sodium, which in the United States is currently 2,400 mg for an adult. Preferably the amount of sodium is no more than three times the RDA, more preferably no more than two times the RDA, and most preferably no more than the RDA for sodium.

In preferred embodiments, the energy-promoting composition is formulated such that the molar ratio of sodium ions to potassium ions is no greater than about 2.5, more preferably no greater than about 2.0, or about 1.5, or even more preferably no greater than about 1.0.

An example of a supplement for providing ketone bodies is goBHB™ manufactured by Compound Solutions, Inc.

B. Vasodilating Component

In some embodiments, the vasodilator component comprises one or more of quercetin, L-citrulline and salts thereof such as citrulline malate, L-arginine and salts thereof, agmatine and salts thereof, nitrates (extracts from beetroot, celery, cress, chervil, lettuce, spinach, arugula), gallic acid, coenzyme Q10 (CoQ10), trimethylglycine, niacin, theanine, theobromine, garlic, magnesium, grape seed extract, green tea extract, catechins and/or epicatechins (e.g., from green tea or and/or grape seed), proanthocyanidins (e.g., galloylated proanthocyanids), arginase inhibitors such as L-norvaline, nitric oxide synthase promoters such as beta-alanine and/or glutathione, and GABA receptor agonists such as taurine. Many of the foregoing vasodilating compounds function at least partially as nitric oxide promoters, though others may involve other primary vasodilating mechanisms.

In general, example monomer catechins and epicatechins have the following formulas and are stereoisomers of each other:

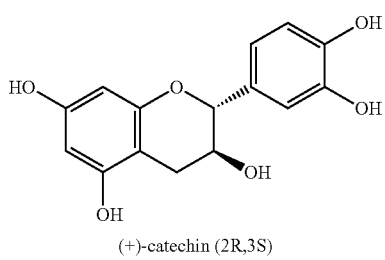
(+)-catechin (2R,3S)

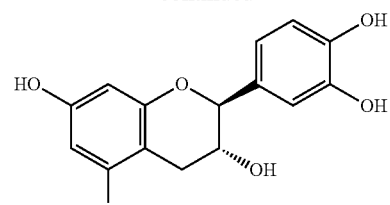
(−)-catechin (2S,3R)

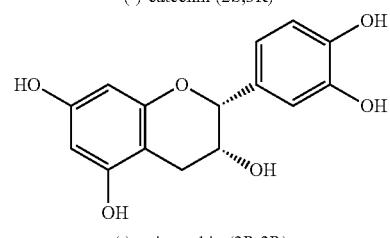
(−)-epicatechin (2R,3R)

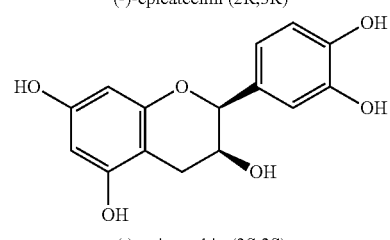
(−)-epicatechin (2S,3S)

Catechins and epicatechins have vasodilating properties and can be used in any combination or derivative, including dimers, trimers, and oligomers thereof. In some embodiments, the vasodilator component includes (−)-epicatechin derivatives, such as epicatechin-(4-8)-epicatechin-(4-8)-epicatechin or epicatechin-(4-8)-epicatechin-(4-8)-epicatechin-gallate, the latter of which is depicted below. Such compounds are described in detail in U.S. Pat. No. 6,706,756, which is incorporated herein by this reference. An example of epicatechin-containing supplement is Vaso 6™ manufactured by Compound Solutions, Inc.

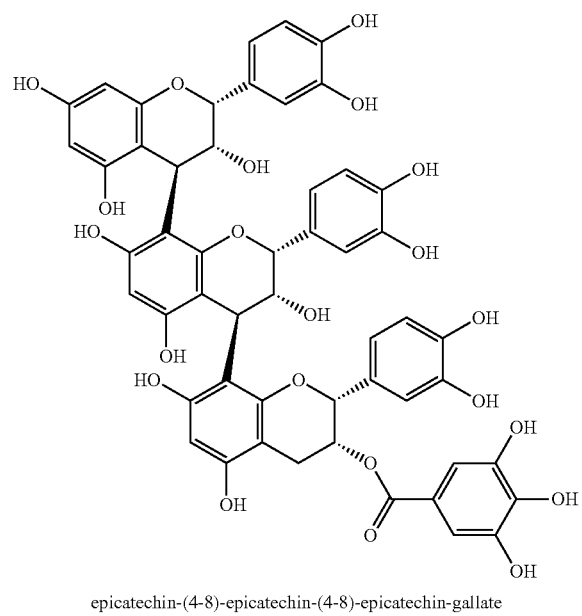 [SMILES: O=C(O[C@@H]1Cc2c(O)cc(O)c([C@H]3c4c(O)cc(O)c([C@H]5c6c(O)cc(O)cc6O[C@H](c6ccc(O)c(O)c6)[C@@H]5O)c4O[C@H](c4ccc(O)c(O)c4)[C@@H]3O)c2O[C@@H]1c1ccc(O)c(O)c1)c1cc(O)c(O)c(O)c1]
epicatechin-(4-8)-epicatechin-(4-8)-epicatechin-gallate

The amount of the vasodilating component included may be varied according to the particular combination of compounds making up the vasodilator component. In some embodiments, the vasodilating component is provided at a functional dose formulated to provide a vasodilating effect equal or substantially similar to a dose of about 1 g to about 8 g citrulline, or about 2 g to about 6.5 g citrulline, or about 3 g to about 5 g citrulline.

Several techniques are known in the art for measuring vasodilation, including those described by Lind et al. "Evaluation of four different methods to measure endothelium-dependent vasodilation in the human peripheral circulation" Clin Sci (Lond), 2002 May; 102(5):561-7; Heiss et al. "In vivo measurement of flow-mediated vasodilation in living rats using high-resolution ultrasound" Am J Physiol Heart Circ Physiol., 2008 February; 294(2):H1086-93; and Yamashita et al. "The effects of vasodilation on cardiac output measured by PiCCO" J Cardiothorac Vasc Anesth. 2008 October; 22(5): 688-92, for example.

C. Stimulant Component

In some embodiments, the stimulant component comprises an effective amount of caffeine, which has no caloric value but can boost mental alertness and metabolism of available caloric energy sources. Caffeine may be included in an amount ranging from about 30 mg to about 250 mg, or about 40 mg to about 225 mg, or about 50 mg to about 200 mg, or about 60 mg to about 180 mg, or about 80 mg to about 160 mg. Caffeine is a preferred stimulant component because it is widely utilized, well understood, well tolerated, easy to dose, and familiar to almost all users.

Unfortunately, caffeine also causes vasoconstriction and other associated effects such as increased blood pressure, which are undesirable for the typical, casual user. As with other stimulants that increase alertness but provide no caloric value, caffeine also tends to have a crash effect where users feel tired and sluggish as the dose is metabolized and wears off.

The stimulant component may additionally or alternatively include other stimulant compounds that increase alertness but provide no caloric value, such as one or more other adenosine receptor antagonists, other phosphodiesterase inhibitors, epinephrine and/or norepinephrine promoters, or combinations thereof. Where such additional or alternative stimulant compounds are utilized, they are preferably provided in an amount such that the combined stimulant composition provides a stimulant effect substantially similar to that provided by caffeine in amounts within the ranges described above.

In some embodiments, the stimulant component includes other xanthine alkaloids in addition to or alternative to caffeine, such as theacrine, theobromine, theophylline, methylliberine, other caffeine analogs, or combinations thereof. While most of these compounds are generally effective stimulants, most are also associated with undesirable vasoconstriction and potential increases in blood pressure, as with caffeine. As an exception, theobromine functions as a very mild vasodilator. Theacrine and methylliberine are believed to be somewhat less vasoconstricting than caffeine, though neither are vasodilators and likely have a mild vasoconstricting effect. Theacrine is often confused with the amino acid theanine, which in contrast does promote vasodilation. An example of methylliberine is Dynamine™ manufactured by Compound Solutions, Inc.

Epinephrine and/or norepinephrine promoters, if utilized in the stimulant component, may include one or more of yohimbine, rauwolscine, Ephedra-based compounds such as ephedrine and pseudoephedrine, synephrine, octopamine, 1,3-dimethylamylamine, higenamine, clenbuterol, and adrenaline/noradrenaline reuptake inhibitors such as hordenine and atomoxetine, for example.

D. Other Components and Aspects of Composition

In some embodiments, the energy-promoting compositions include ketone bodies as the primary or sole caloric energy source by omitting glucose or other sugars, such as fructose, sucrose, or other simple sugars that the body readily converts to glucose. Excess glucose can rapidly take the user out of ketosis, where the ketone bodies are primarily used as the cellular fuel, and causes a return to glycolysis, where glucose is the primary cellular fuel. In glycolysis, the user may be unable to reap the full benefits of the ketone body energy source. Rather, the crash effect may be exacerbated by the postprandial hypoglycemia (i.e., "sugar crash"). Some so-called energy drinks go so far as replacing sugar with artificial sweeteners, which means they contain no actual caloric energy but only a stimulant such as caffeine, which increases alertness but provides no caloric energy.

The energy-promoting composition may optionally include a nootropic component formulated to promote cognition, mood, and/or focus, and can thereby also aid in attenuating the crash effect of the stimulant component, in particular the drop in levels of dopamine and/or acetylcholine. In some embodiments, the nootropic component may include one or more of a dopamine promoter (including dopamine precursors, dopamine receptor agonists and/or dopamine breakdown or reuptake inhibitors), an acetylcholine promoter (including acetylcholine precursors, acetylcholine receptor agonists, acetylcholinesterase inhibitors, and/or acetylcholine reuptake inhibitors), and/or other nootropic compound(s).

A suitable dopamine promoter may include methylliberine, theacrine, *Mucuna pruriens*, tyrosine, L-DOPA (i.e., L-3,4-dihydroxyphenylalanine), phenylalanine, phenylethylamine, tolcapone, or a combination thereof. A suitable acetylcholine promoter may include huperzine-A (toothed clubmoss extract (aerial parts) from *Huperzia serrata*), acetylcholinesterase inhibitor), dimethylaminoethanol, choline, alpha-glycerophosphocholine, uridine, citicoline, racetams such as piracetam, phenylpiracetam, oxiracetam, and aniracetam, or a combination thereof.

The nootropic component may additionally or alternatively include one or more other nootropic compounds such as a serotonin promoter (e.g., tryptophan, 5-hydroxytryptophan (5-HTP)), beta-al anine, D-serine, phosphatidylserine, *Panax ginseng, Ginkgo biloba, Rhodiola rosea, Polygala tenuifolia, Muira puama, Eschscholzia californica, Convolvulus pluricaulis, Centella asiatica, Evolvulus alsinoides, Bacopa monnieri, Epimedium* herbs, *Ashwagandha* herbs, a cyclic adenosine monophosphate (cAMP) modulator such as forskolin or vinpocetine, or a combination thereof.

The energy-promoting composition may optionally include a medium chain fatty acid, salt, or ester thereof in as a supplementary source of endogenous ketone bodies that can provide caloric energy in addition to beta-hydroxybutyrate supplementation. Medium chain fatty acids, salts, or mono-, di-, or triglycerides thereof can be converted by the body into endogenous ketone bodies. Medium chain fatty acids have from 6 to 12 carbons, preferably from 8 to 10 carbons (e.g., caproic acid, caprylic acid, capric acid, and lauric acid).

Though possibly adversely affecting taste, the energy-promoting composition may optionally include a short chain fatty acid, salt or ester thereof, or a mono-, di- or triglyceride of the at least one short chain fatty acid. Short chain fatty acids have less than 6 carbons (e.g., acetic acid, propionic acid, butyric acid, isobutyric acid, valeric acid, and isovaleric acid). An example short chain triglyceride is tributyrin. Such molecules can provide protection to the gut and improve microbiome health.

The energy-promoting compositions may include flavorings that enhance the taste. Examples include sweeteners (e.g., *stevia* extract, such as Rebaudioside A), fruit flavors, mint flavors, other natural flavors, and the like.

Other optional additives include thickeners (e.g., xanthan gum), emulsifiers, preservatives, flow agents (e.g., silicon dioxide), beet root powder, beta carotene, vitamins (e.g., A, C, D, E, niacin, B6, folate, B12), minerals (e.g., iodine, magnesium, zinc, copper, manganese, chromium, fruit extracts, vegetable extracts, enzymes (e.g., amylase, cellulase, lactase, lipase, protease), legume extracts, and the like.

III. Actions and Effects of the Energy-Promoting Compositions

FIG. 1 is a flow chart that illustrates the interactive beneficial effects between the major components of the energy-promoting composition. The combination of an exogenous ketone body component that provides useable and reliable source of caloric energy, a vasodilator component, and a stimulant component (which increases mental alertness and can increase metabolism of available caloric energy but provides no caloric energy itself) in a single formulation provides benefits not obtainable from a composition that include only one or two of the components.

The ketone body component affects the action of stimulant component by attenuating the crash effect of the stimulant component. Inclusion of the ketone body component has been found to beneficially smooth out and/or prolong the experienced energy levels of the user. For example, as compared to a similar composition that omits ketone bodies or that replaces them with a sugar ingredient such as fructose, glucose, or sucrose as a caloric energy source, users report experiencing more sustained and smooth energy levels after consuming an energy-promoting composition containing the ketone body component.

As shown, the vasodilator component beneficially functions to improve the pharmacokinetic distribution of both the ketone body component and the stimulant component. In other words, the vasodilator component may function to increase blood flow to peripheral tissues of the body so that the ketone bodies and the stimulant compound(s) can more effectively move from the digestive system to their intended targets (e.g., brain and muscle tissues).

The vasodilator component also functions to counteract any vasodilating effects of the stimulant component. Most stimulants, including caffeine, cause vasoconstriction and associated increases in blood pressure. This can be harmful to the cardiac and vascular system. Moreover, vasoconstriction reduces blood flow and thereby lowers the efficiency of pharmacokinetic delivery of the energy-promoting composition to the peripheral tissues of the body. The vasodilator component beneficially counteracts the negative vasoconstricting effects to the vascular and cardiac systems, and likewise functions to maintain effective blood flow for more efficient delivery of the energy-promoting composition to the peripheral tissues of the body.

The stimulant component, which is not itself a source of caloric energy, beneficially interacts with the ketone body component by enhancing pharmacokinetic absorption and uptake of the ketone bodies into the tissues so it can be readily utilized as a caloric energy source. In other words, the stimulant component has been found to increase the efficiency in which the ketone body component is actually taken into cells and metabolized as caloric energy.

FIG. 1 therefore illustrates the interconnected and interactive nature of the individual components of the energy-promoting composition when combined. Each individual component enhances the beneficial effects and/or reduces the negative effects of one or both of the other components such that the combination as a whole beneficially provides a greater effect than each component individually or even two of the components combined.

Figure 2:
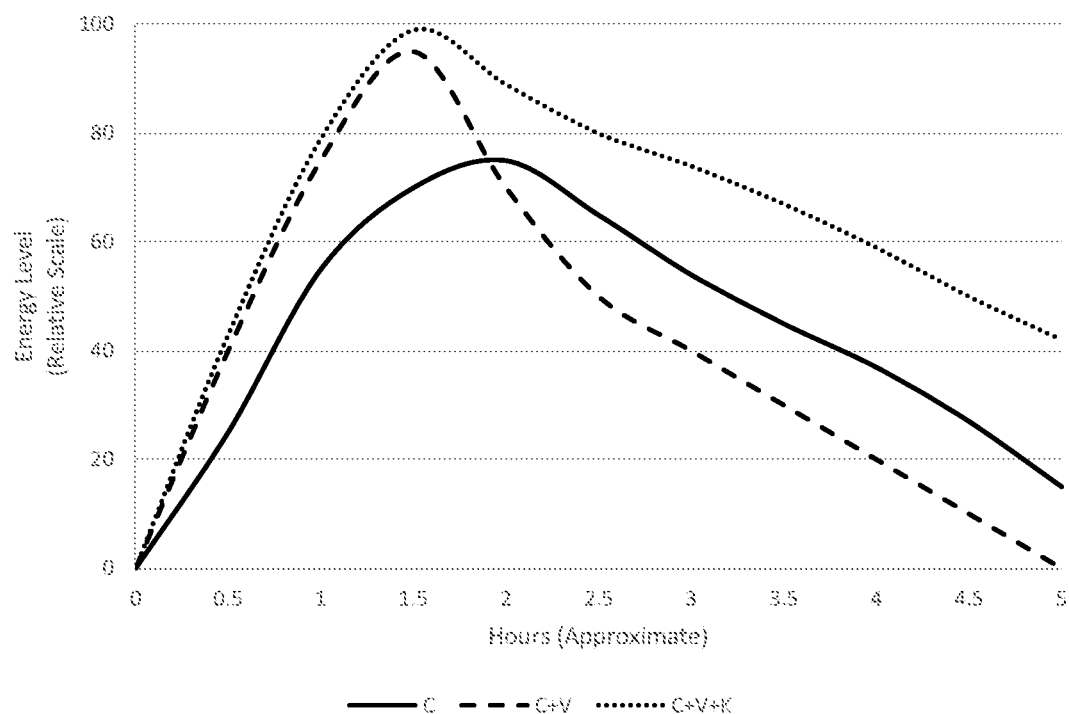
FIG. 2 is a chart that graphically illustrates the expected differences in perceived energy levels experienced by a typical user when consuming a composition including caffeine ("C"), an otherwise similar composition including caffeine and a vasodilator component ("C+V"), and an otherwise similar composition including a ketone body component, a vasodilator component, and caffeine ("C+V+K") according to the invention.

FIG. 2 is a chart that illustrates the expected and observed differences in energy levels experienced by a typical user when consuming a composition including caffeine ("C"), an otherwise similar composition including caffeine and a vasodilator component ("C+V"), and an otherwise similar composition including caffeine, a vasodilator component, and a ketone body component ("C+V+K") according to the invention. In FIG. 2, "energy level" means the level of mental and physical alertness experienced by the user, not the amount of actual caloric energy provided by the various components. Stimulants such as caffeine provide no actual caloric energy.

As shown, the C+V composition produces a higher and faster experienced energy peak as compared to the C composition by itself, which is due to the enhanced blood flow and enhanced delivery of caffeine to peripheral tissues, which enhances mental alertness and metabolism of available energy sources. However, the C+V composition may induce a more pronounced crash than the C composition by itself for the same reasons it provides a more pronounced onset of effects.

In contrast, the C+V+K composition provides energy levels experienced by the user that substantially track the C+V composition initially. However, where the energy provided by the C+V composition begins to drop sharply, the C+V+K composition maintains a more sustained energy level due to the crash attenuating and energy sustaining properties of the caloric energy and other metabolic benefits provided by the ketone body component. The overall result is that the C+V+K composition provides the benefits of rapid onset and high peak in experienced energy, coupled with higher actual overall energy levels over time, which minimizes the crash effect relative to the C and C+V compositions.

IV. Delivery Methods and Dosage Forms

The energy-promoting composition may be consumed or administered through any acceptable administration route. In preferred embodiments, the composition is formulated for oral consumption as a liquid "energy drink" or "energy shot." The liquid formulation may include other suitable ingredients such as flavoring agents, water, carbonated water, pH modifiers (e.g., phosphoric acid, citric acid, malic acid, tartaric acid, or succinic acid), preservatives (e.g., benzoate and/or sorbate salts), and sweeteners (e.g., sucralose, *stevia* saccharin, aspartame). In other embodiments the composition may be formulated as a capsule, tablet (e.g., dissolvable tablet), lozenge, powder, candy (e.g., gummy, sucker, pastille), gel, paste, mouth spray, or other dosage form suitable for oral administration. A composition having an acidic pH (e.g., between 4-5) may be desirable as a preservative and/or to provide a desirable tart or sour taste. When a beta-hydroxybutyrate mixed salt-acid and/or acetoacetate mixed salt-acid is/are used, it may be possible to manufacture a composition having a desired acidic pH such that an additional pH modifier (e.g., acid) may be reduced or eliminated.

When formulated as a liquid, the energy-promoting composition may be provided in a can, bottle, flask, or other such container configured to hold a desired number of unit doses of the composition. A container may hold, for example, about 2 ounces to about 40 ounces of the energy-promoting composition, more typically about 2.5 ounces to 24 ounces or about 3 ounces to about 12 ounces. The separate components of the energy-promoting composition may be diluted or concentrated accordingly so as to provide desired levels of each component in each corresponding unit dose of the container. For example, a smaller "shot" may be more concentrated than a larger and more dilute drink.

A method of delivering an energy-promoting composition to a user may include the steps of: 1) providing an energy-promoting composition comprising a caloric energy source including a ketone body component a vasodilator component, a stimulant component that increases alertness, and optionally a nootropic component; and 2) administering the energy-promoting composition to the user to thereby support an energy level of the user. In most if not all cases, the vasodilator, stimulant, and nootropic components do not provide caloric energy.

An energy-promoting composition may be taken as needed to promote higher energy levels, to reduce fatigue, to enhance mental focus, and/or to improve mood. In some implementations it may be taken daily or in multiple doses (e.g., 2, 3, 4 or more) spread throughout the day.

V. Examples

The following is a description of exemplary energy-promoting compositions useful for promoting higher energy levels, reducing fatigue, enhancing focus, and/or improving mood.

Example 1

| | |
|---|---|
| Sodium beta-hydroxybutyrate | 1 g |
| Potassium beta-hydroxybutyrate | 1 g |
| Magnesium beta-hydroxybutyrate | 1 g |
| Calcium beta-hydroxybutyrate | 1 g |
| Caffeine | 120 mg |
| Epicatechins | 500 mg |
| Huperzine-A | 200 mcg |
| Citric acid (pH modifier) | to yield pH of 5.5 |
| Flavorings | to taste |
| Water | 120 ml |

The energy-promoting composition is a drink.

Example 2

| | |
|---|---|
| Sodium beta-hydroxybutyrate mixed salt-acid | 1 g |
| Potassium beta-hydroxybutyrate mixed salt-acid | 1 g |
| Magnesium beta-hydroxybutyrate mixed salt-acid | 1 g |
| Calcium beta-hydroxybutyrate mixed salt-acid | 1 g |
| Caffeine | 120 mg |
| Epicatechins | 500 mg |
| Huperzine-A | 200 mcg |
| Flavorings | to taste |
| pH | 5.5 |
| Water | 120 ml |

The energy-promoting composition is a drink.

Example 3

| | |
|---|---|
| Sodium beta-hydroxybutyrate mixed salt-acid | 0.35 g |
| Potassium beta-hydroxybutyrate mixed salt-acid | 2.65 g |
| Magnesium beta-hydroxybutyrate mixed salt-acid | 0-2.5 g |
| Calcium beta-hydroxybutyrate mixed salt-acid | 0-2.5 g |
| Caffeine | 150 mg |
| Methylliberine (Dynamine ™) | 26 mg |
| Epicatechins (Vaso 6 ™) | 50 mg |
| Huperzine-A | 750 mcg |
| Citric acid (pH modifier) | |
| Malic Acid (pH modifier) | |
| Phosphoric Acid (pH modifier) | |
| pH | 5.5 |
| Flavorings | |
| Sucralose | |
| Potassium Sorbate | |
| Sodium Benzoate | |
| Acesulfame Potassium | |
| Water | to make 90 mL |

The energy-promoting composition is a drink

Example 4

Any of the foregoing examples is modified to make a powder that can be added to water or other liquid to form a drink.

The claimed invention may be embodied in other specific forms without departing from its spirit or essential characteristics. The described embodiments are to be considered in all respects only as illustrative and not restrictive. The scope of the claimed invention is, therefore, indicated by the appended claims rather than by the foregoing description. All changes that come within the meaning and range of equivalency of the claims are to be embraced within their scope.

The invention claimed is:

1. An energy-promoting composition, comprising:
   an exogenous ketone body component that provides a source of caloric energy;
   a vasodilator component; and
   a stimulant component that increases alertness, provides no source of caloric energy, and optionally increases metabolism of available caloric energy.

2. The energy-promoting composition of claim 1, wherein the exogenous ketone body component comprises at least one of beta-hydroxybutyric acid, a beta-hydroxybutyrate salt, a beta-hydroxybutyrate ester, acetoacetic acid, an acetoacetate salt, or an acetoacetate ester.

3. The energy-promoting composition of claim 1, wherein the exogenous ketone body component is included in an amount ranging from about 0.5 g to about 20 g, or about 1 g to about 15 g, or about 2 g to about 10 g, or about 3 g to about 8 g.

4. The energy-promoting composition of claim 1, wherein the exogenous ketone body component comprises a mixed salt-acid including beta-hydroxybutyric acid and at least one salt selected from the group consisting of magnesium beta-hydroxybutyrate, calcium beta-hydroxybutyrate, sodium beta-hydroxybutyrate, and potassium beta-hydroxybutyrate.

5. The energy-promoting composition of claim 1, wherein the vasodilator component comprises one or more of a nitric oxide promoter, an arginase inhibitor, and a nitric oxide synthase promoter.

6. The energy-promoting composition of claim 1, wherein the vasodilator component is selected from the group consisting of quercetin, L-citrulline, L-citrulline salts, L-arginine, L-arginine salts, agmatine, agmatine salts, nitrates, gallic acid, coenzyme Q10 (CoQ10), trimethylglycine, niacin, theanine, theobromine, garlic, magnesium, grape seed extract, green tea extract, catechins, epicatechins, cacao, proanthocyanidins, galloylated proanthocyanidins, L-norvaline, beta-alanine, glutathione, taurine, and combinations thereof.

7. The energy-promoting composition of claim 6, wherein the vasodilator component comprises at least one of niacin, theanine, catechin, or epicatechin.

8. The energy-promoting composition of claim 1, wherein the vasodilator component is included at a dose formulated to provide a vasodilating effect equal or substantially similar to a dose of about 1 g to about 8 g citrulline, or about 2 g to about 6.5 g citrulline, or about 3 g to about 5 g citrulline.

9. The energy-promoting composition of claim 1, wherein the stimulant component comprises one or more adenosine receptor antagonists, phosphodiesterase inhibitors, epinephrine and/or norepinephrine promoters, or combinations thereof.

10. The energy-promoting composition of claim 1, wherein the stimulant component comprises one or more xanthine alkaloids selected from the group consisting of caffeine, theacrine, theobromine, theophylline, methylliberine, and caffeine analogs.

11. The energy-promoting composition of claim 1, wherein the stimulant component comprises methylliberine.

12. The energy-promoting composition of claim 1, wherein the composition omits glucose, fructose, and sucrose.

13. The energy-promoting composition of claim 1, further comprising a nootropic component.

14. The energy-promoting composition of claim 13, wherein the nootropic component comprises one or more of *Mucuna pruriens*, tyrosine, L-DOPA (i.e., L-3,4-dihydroxyphenylalanine), huperzine-A, dimethylaminoethanol, phenylalanine, phenylethylamine, choline, alpha-glycerophosphocholine, uridine, citicoline, a racetam, or a combination thereof.

15. The energy-promoting composition of claim 13, wherein the nootropic component comprises one or more of tryptophan, 5-hydroxytryptophan (5-HTP), D-serine, phosphatidylserine, *Panax ginseng, Ginkgo biloba, Rhodiola rosea, Polygala tenuifolia, Muira puama, Huperzia serrata, Eschscholzia californica, Convolvulus pluricaulis, Centella asiatica, Evolvulus alsinoides, Bacopa monnieri, Epimedium* herbs, *Ashwagandha* herbs, forskolin, vinpocetine, or a combination thereof.

16. The energy-promoting composition of claim 1, wherein the composition is formulated as a consumable liquid.

17. An energy-promoting composition, comprising:
    water;
    a caloric energy source comprising an exogenous ketone body component selected from beta-hydroxybutyric acid, beta-hydroxybutyrate salt, or beta-hydroxybutyrate ester;
    a vasodilator component comprising at least one of niacin, theanine, a catechin, or an epicatechin; and
    a stimulant component that increases alertness, provides no source of caloric energy, and optionally increases metabolism of available caloric energy.

18. The energy-promoting composition of claim 17, wherein the stimulant component comprises at least one of methylliberine or caffeine.

19. An energy-promoting composition, comprising:
    one or more exogenous ketone body components that provide caloric energy;
    a vasodilator component selected from the group consisting of quercetin, L-citrulline, L-citrulline salts, L-arginine, L-arginine salts, agmatine, agmatine salts, nitrates, gallic acid, coenzyme Q10 (CoQ10), trimethylglycine, niacin, theanine, theobromine, garlic, magnesium, grape seed extract, green tea extract, catechins, epicatechins, cacao, proanthocyanidins, galloylated proanthocyanidins, L-norvaline, beta-alanine, glutathione, taurine, and combinations thereof;
    a stimulant component that increases alertness, optionally increases metabolism of available caloric energy, and is selected from the group consisting of caffeine, theacrine, theophylline, and methylliberine; and
    a nootropic component different than the stimulant component selected from the group consisting of *Mucuna pruriens*, tyrosine, L-DOPA (i.e., L-3,4-dihydroxyphenylalanine), huperzine-A, dimethylaminoethanol, phenyl-alanine, phenylethylamine, choline, alpha-glycerophosphocholine, uridine, citicoline, tryptophan, 5-hydroxytryptophan (5-HTP), D-serine, phosphatidylserine, *Panax ginseng, Ginkgo biloba, Rhodiola rosea, Polygala tenuifolia, Muira puama, Huperzia serrata, Eschscholzia californica, Convolvulus pluricaulis, Centella asiatica, Evolvulus alsinoides, Bacopa monnieri, Epimedium* herbs, *Ashwagandha* herbs, forskolin, vinpocetine, and combinations thereof.

20. The energy-promoting composition of claim 1, further comprising a ketone body precursor selected from 1,3-butanediol or ester of 1,3-butanediol.

* * * * *